United States Patent
Guala et al.

[19]

[11] Patent Number: 6,161,812
[45] Date of Patent: Dec. 19, 2000

[54] CLAMP FOR CLOSING FLEXIBLE HOSES OF INFUSION TRANSFUSION AND THE LIKE MEDICAL EQUIPMENT

[75] Inventors: Gianni Guala; Ernesto Guala, both of Turin, Italy

[73] Assignee: Industrie Borla SpA, Turin, Italy

[21] Appl. No.: 09/227,710

[22] Filed: Jan. 8, 1999

[30] Foreign Application Priority Data

Oct. 22, 1998 [EP] European Pat. Off. .............. 98830632

[51] Int. Cl.[7] ................................................... F16L 55/14
[52] U.S. Cl. ................................................ 251/10; 251/9
[58] Field of Search ............................................ 251/10, 9

[56] References Cited

U.S. PATENT DOCUMENTS

| 3,822,052 | 7/1974 | Lange . | |
|---|---|---|---|
| 4,235,412 | 11/1980 | Rath et al. | 251/10 |
| 4,588,160 | 5/1986 | Flynn et al. | 251/10 |
| 4,589,626 | 5/1986 | Kurtz et al. | 251/10 |
| 5,035,399 | 7/1991 | Rantanen-Lee | 251/10 |
| 5,203,056 | 4/1993 | Funk et al. . | |
| 5,810,792 | 9/1998 | Fangrow, Jr. et al. . | |

FOREIGN PATENT DOCUMENTS

| 0 637 456 | 2/1995 | European Pat. Off. . |
|---|---|---|
| 3908181 | 9/1990 | Germany . |

*Primary Examiner*—Kevin Shaver
*Assistant Examiner*—John Bastianelli
*Attorney, Agent, or Firm*—Sughrue, Mion, Zinn, Macpeak & Seas, PLLC

[57] ABSTRACT

A resilient clamp comprises a body forming in one single piece an upper arm and a lower arm connected to each other at one side by a springing curved end portion and provided at the other side with an anchoring element and an anchoring member, respectively, which are mutually releasably snap engageable. The upper arm has a manoeuvre portion super-elevated with respect to the anchoring element. Further structural features of the body afford reducing the closing effort and minimizing any risks of unintentional opening of the clamp.

7 Claims, 3 Drawing Sheets

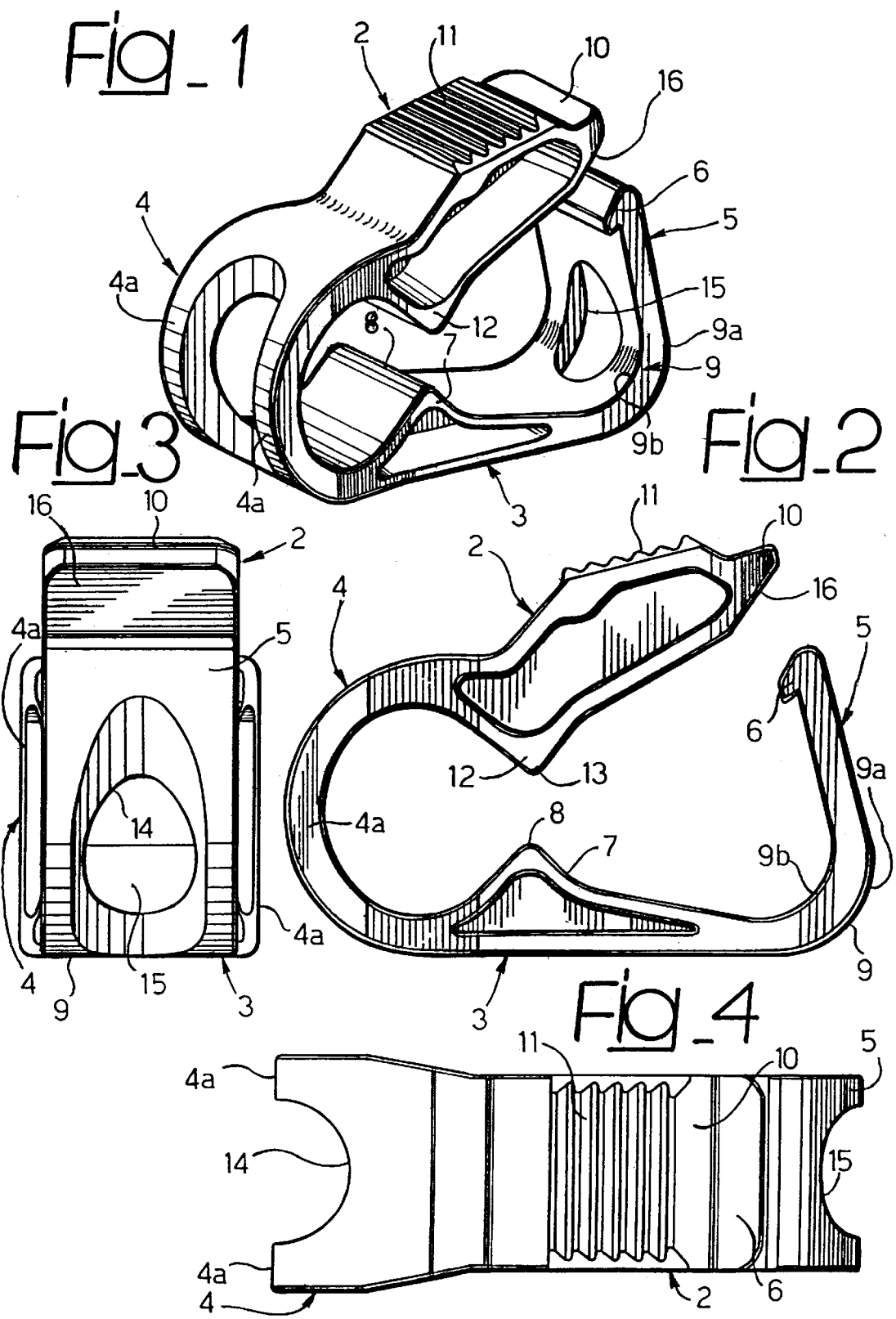

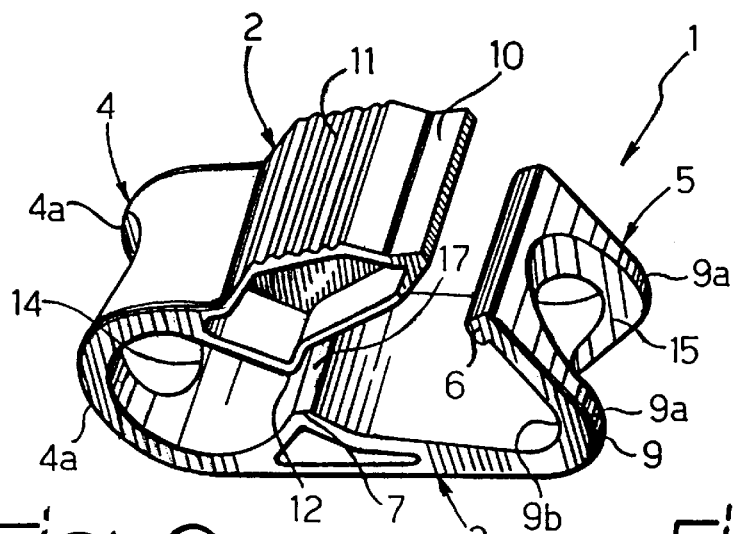
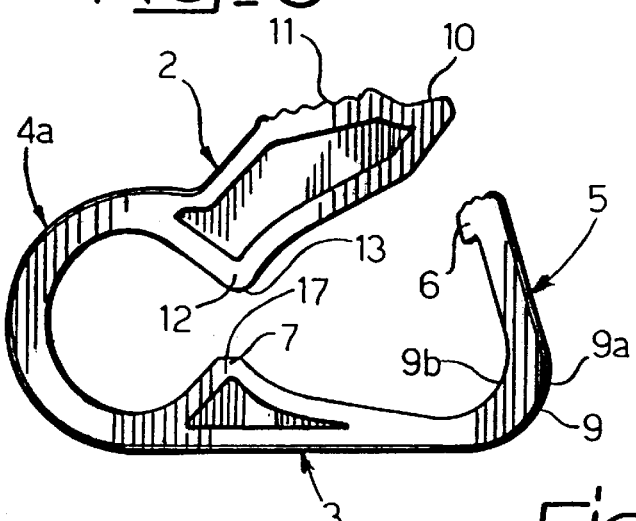
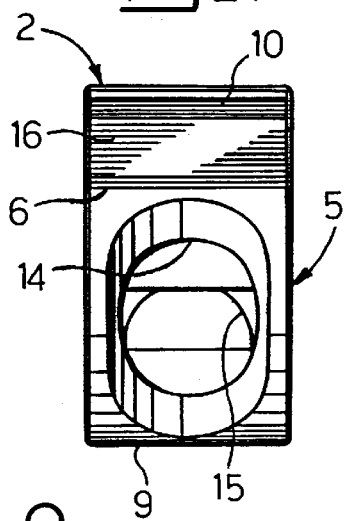
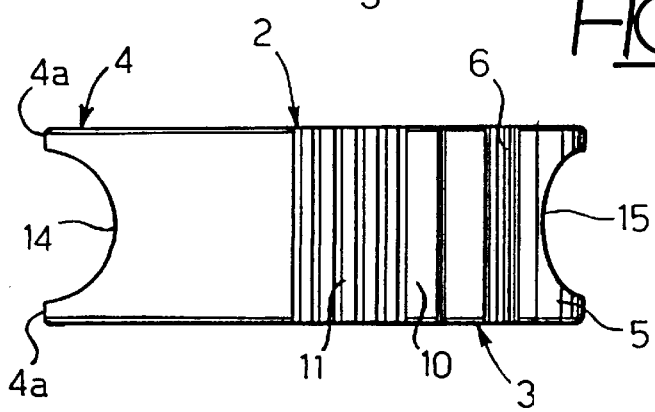

6,161,812

CLAMP FOR CLOSING FLEXIBLE HOSES OF INFUSION TRANSFUSION AND THE LIKE MEDICAL EQUIPMENT

BACKGROUND OF THE INVENTION

The present invention is generally related to resilient clamps for closing flexible hoses of infusion, transfusion and the like equipment.

More particularly the invention is directed to a resilient clamp of the type comprising a body forming in one single piece an upper arm, a lower arm and a curved end portion having a substantially semi-circular shape and elastically interconnecting the upper and lower arms. The lower arm is provided on its side opposite to the curved end portion of the body with an elastic branch bent towards the upper arm and having an anchoring member, and the upper arm is provided, also on its side opposite to said curved end portion of the body, with a maneuver portion and an anchoring element complementary to said anchoring member of the elastic branch of the lower arm and releasably engageable with the anchoring member. The upper and lower arms are further formed with respective juxtaposed clamping projections facing towards the inside of the body and displaceable between a mutually distal position, corresponding to a disengaged condition between said anchoring member and said anchoring element, and a mutually proximal position corresponding to an engaged condition between said anchoring member and said anchoring element. The curved end portion of the body and the elastic branch of the lower arm are formed with respective apertures defining a passageway for a flexible hose fitted through the body between said upper and lower arms.

Resilient clamps of the above-referenced type are since long produced and successfully marketed by the Applicant. In use, in order to perform clamping of the hose fitted through the clamp body, it is sufficient to press a finger onto the maneuver portion of the upper arm, so as to bring it near to the lower arm by virtue of the elastic deformation of the curved end portion of the body, up to engagement between the anchoring element and the anchoring member, due to their mutual snap coupling following elastic deflection outwardly of the bent branch of the lower arm. This operation produces displacement of the inner clamping projections of the upper arm and of the lower arm from their distal position to their proximal position, thus clamping and throttling the flexible hose.

The conventional clamps of the above referenced type are affected by several drawbacks from both the functional and ergonomical point of view, i.e. in connection with operating thereof by the user. These drawbacks derive from a partially inadequate structural conformation of these known clamps owing to the reasons listed in the following.

Firstly, in the known clamps the maneuver portion of the upper arm is located flush with or in any case substantially at the same level of the anchoring element carried by the upper arm. In use, in case the nail of the user's finger pressing against the manoeuvre portion is projecting beyond the end of the upper arm, upon snap engagement between the anchoring element and the anchoring member the nail itself may be broken, with an evidently painful consequence. Moreover, for the same reason, in the engaged condition between the anchoring element and the anchoring member the elastic branch of the lower arm is projecting above the upper arm and is thus exposed to the risk of accidental disengagement.

Secondly in the above conventional resilient clamps the clamping projections for the flexible hose are located substantially in correspondence of the centre of the body, whereby the lever arms on which the user's thrust is applied, i.e. the portions of the upper arm and of the lower arm comprised between the respective clamping projections—reacting against the hose—and the anchoring element and anchoring member, respectively, are relatively short, which involves a relatively important effort by the user himself to perform snap closing of the clamp.

Thirdly in the known clamps the bent elastic branch of the lower arm is connected thereto through a curved portion having a relatively great curvature radius, and such that this bent elastic branch is oriented substantially perpendicularly to the lower arm. With this arrangement in the closed condition of the clamp, namely when the flexible hose fitted through the body is clamped, the elastic reaction provided by the anchoring member carried by the bent branch of the lower arm is relatively weak, which extends the risk of accidental opening under the elastic return action applied by the clamped hose against the clamping projections.

Lastly, in the known resilient clamps the curved end portion of the body connecting the lower arm and the upper arm to each other has a limited mass due in part to its reduced thickness and in part to the presence of the aperture for the hose passing through. This involves on one side a limited elastic reaction in the closed condition of the clamp, and on the other side risks of twistings and also of breakages upon closing the clamp itself.

SUMMARY OF THE INVENTION

The object of the present invention is to overcome the above inconveniences.

These objects are achieved, according to the invention, by a resilient clamp of the type defined at the beginning the main feature of which resides in that said maneuver portion of the upper arm is superelevated with respect to said anchoring element.

By virtue of this solution a first advantage is afforded, consisting of that closing operation of the clamp does not involve any risks for integrity of the user's finger since his/her nail is constantly maintained, while the anchoring element and the anchoring member are mutually snap engaged with each other, at a level which is well above the anchoring element. Moreover, in the closed condition of the clamp, the superelevated maneuver portion provides a front protection for the anchoring element, which prevents unintentional or accidental disengagement thereof relative to the anchoring member.

According to another feature of the invention, between said lower arm and said bent elastic branch thereof a curved section is provided having a curvature radius such that said bent elastic branch forms with said lower arm, in an indeformed condition, an acute angle.

This arrangement enables achieving a second advantage, consisting of that in the closed condition of the resilient clamp, i.e. in the engaged condition between the anchoring element and the anchoring member, the elastic reaction against opening provided by the anchoring member is appreciably enhanced, which further contributes to prevent any risks of undesired clamp opening.

According to a further feature of the invention the distance between the clamping projection of the upper arm and said anchoring element is substantially greater than the distance between said clamping projection of the upper arm and said curved end portion of the body. Likewise, the distance between the clamping projection of the lower arm and said bent resilient branch thereof is substantially greater than the distance between said clamping projection of the lower arm and said curved end portion of the body.

In practice by virtue of this arrangement the throttling area of the flexible hose fitted in use through the clamp, and defined by the two juxtaposed clamping projections, is provided noticeably more backwards with respect to the anchoring member and the anchoring element, i.e. in other words the lever arms for mutual snap engagement between the anchoring element and the anchoring member, and more particularly that corresponding to the upper arm with its manoeuvre portion, are remarkably longer, which reduces as a consequence the user's effort required to close the resilient clamp.

According to still another feature of the invention said curved section of the body may conveniently have an outer surface and an inner surface provided with a greater and respectively a lower curvature radius. This feature allows provision of a more relevant mass, and thus of a more relevant elastic reaction, in correspondence of a body area having a relatively reduced thickness and also partly weakened by the presence of the passageway for the flexible hose.

To further enhance strength while reducing any risks of clamp twisting, according to the invention said curved end portion of the body may have a width greater than the width of the upper and lower arms. This arrangement is to be considered preferred in the case of clamps having a small size.

Further advantages achieved by the novel and unique arrangement of the resilient clamp according to the invention reside in improved ergonomics, enhanced convenience of introduction of the flexible hose to be clamped, remarkable lightness and improved strength.

BRIEF DESCRIPTION OF THE DRAWINGS

The invention will now be disclosed in detail with reference to the accompanying drawings, purely provided by way of non limiting example, in which:

FIG. 1 is a diagrammatic perspective view showing a resilient clamp according to a first embodiment of the invention, depicted in its open position, FIG. 2 is an enlarged lateral elevational view of FIG. 1, FIG. 3 is a front elevational view of FIG. 1, FIG. 4 is a top plan view of FIG. 1, FIG. 6 is a perspective view in a reduced scale of a second embodiment of the resilient clamp according to the invention, FIG. 7 is a front elevational view of FIG. 6, FIG. 8 is a top plan view of FIG. 6, and FIG. 9 is a lateral elevational view of FIG. 6.

DETAILED DESCRIPTION OF THE INVENTION

Figure 5:
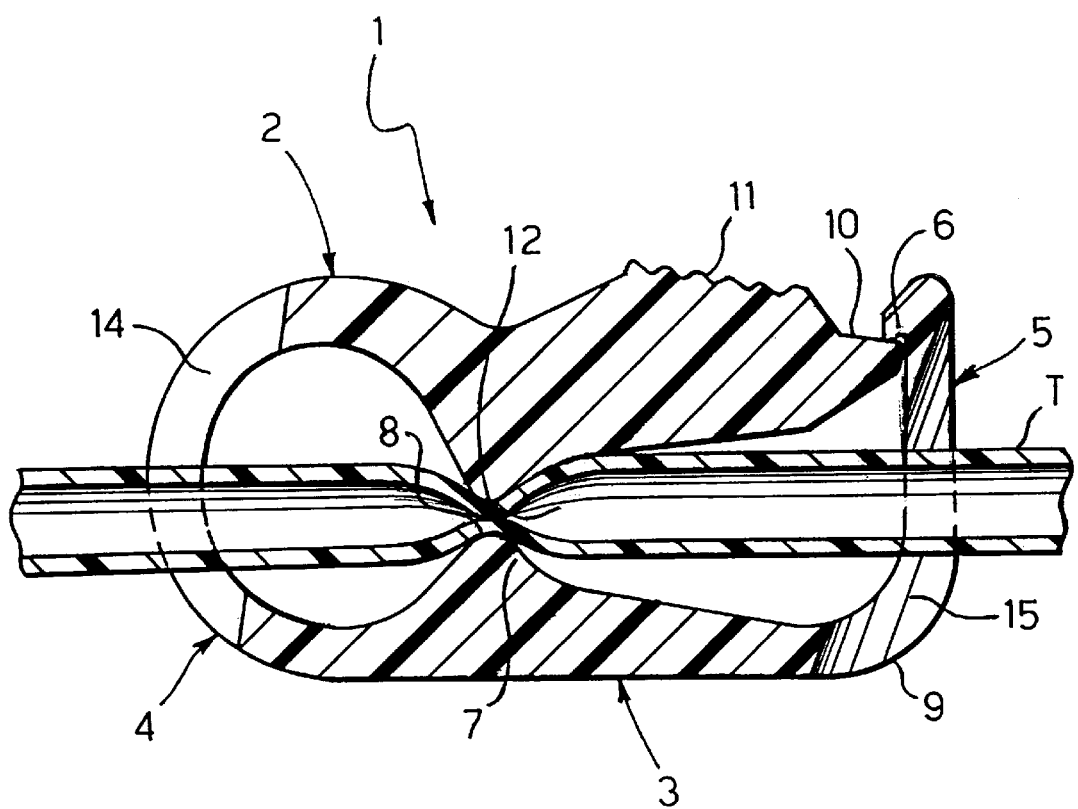
FIG. 5 is a longitudinally sectioned view showing the clamp of FIGS. 1 through 4 in the closed condition while clamping a flexible hose.

FIGS. 1 through 5 show a first embodiment of the resilient clamp according to the invention. This embodiment is to be considered as the preferred mode to carry out the invention in the case of clamps of small size, i.e. having a total length of less than 30 mm. According to this embodiment the clamp comprises a body 1 made of moulded plastic material forming in one single piece an upper arm 2 and a lower arm 3 connected to each other in a mutually springing fashion through a curved end portion 4 having a generally semi-circular shape.

The lower arm 3 is formed, on the side opposite to the curved end 4, with an elastic branch 5 which is bent towards the side of the upper arm 2 and whose free end is provided with an anchoring tooth member 6 projecting towards the inside of the body 2.

Moreover the lower arm 3 is provided, in immediate proximity to the curved end 4, with a transverse clamping projection 7 facing towards the upper arm 2. The top 8 of the clamping projection 7 is preferably rounded.

As it can be better seen in FIG. 2 the elastic branch 5 is connected to the lower arm 2 through a curved section 9 having a curvature radius globally reduced, and such that the angle comprised between the elastic branch 5 and the lower arm 3 is acute, i.e. less than 90°.

Actually, the walls of the curved section 9 have a differentiated curvature radius. More particularly its outer surface 9a has a greater curvature radius, and its inner surface 9b has a lower curvature radius.

As also clearly depicted in FIG. 2, the distance between the clamping projection 8 and the elastic branch 5 is substantially greater, and almost double, than the distance between the clamping projection 7 and the curved end 4 of the body 1.

The upper arm 2 is formed at its free end with an anchoring element 10 complementary with the anchoring member 6 and designed to co-operate with the latter, such as disclosed in the following, upon closing of the resilient clamp. Beneath the anchoring element 10, the free end of the upper arm 2 is provided with a bevelled slanting portion 16.

In the open condition of the clamp shown in FIGS. 1 through 4, in which the body 1 is indeformed, the anchoring element 10 and the bevelled portion 16 are placed above the anchoring member 6, and the clamping projections 7,12 are located in a mutually distal position.

Reference numeral 11 designates a maneuver portion of the upper arm 2, by means of which the clamp can be conveniently set in a closed position. This maneuver portion 11 has a knurled anti-skid surface and is placed in a superelevated position with respect to the anchoring element 10.

The upper arm 2 is further formed on its inner side with a clamping projection 12 facing towards the inside of the body 2 and juxtaposed to the clamping projection 7 of the lower arm 3. The top of the clamping projection 12, designated as 13, has preferably also a rounded design.

The distance between the clamping projection 12 and the anchoring element 10 is substantially greater, and almost double, than the distance between the clamping projection 12 and the curved end 4 of the body 1.

The curved end portion 4 is formed with a wide through aperture 14, whose outer edge is bevelled, allowing introduction of a flexible hose (diagrammatically shown as T in FIG. 5) of an infusion, transfusion or the like medical equipment which in use is longitudinally fitted through the body 1 between the upper arm 2 and the lower arm 3 and exits therefrom through a central through opening 15 of the bent elastic branch 5.

Thus in practice the curved end portion 4 is defined by two arcuated bridges 4a having a reduced thickness but anyway generally greater than the thickness of the resilient clamps according to the prior art. To the aim of enhancing both strength and elastic reaction of these bridges 4a, the invention provides in the case of the embodiment shown in FIGS. 1 through 5, and as already previously explained more specifically related to a resilient clamp having a small size, that the curved end portion 4 as a whole has a greater width than the width of the upper and lower arms 2,3, such as clearly depicted in FIGS. 3 and 4. This arrangement moreover provides an enhanced resistance of the resilient clamp as a whole to lateral yielding and twisting upon closing thereof.

The closing operation is simply performed applying with one finger a pressure onto the maneuver portion 11 of the upper arm 2, so as to depress the latter towards the lower arm 3 due to elastic deformation of the curved end portion 4. Owing to this depression the bevelled portion 16 is brought into contact with the free end of the bent elastic branch 5 thus causing elastic outward deflection thereof up to snap engagement of the anchoring member 6 over the anchoring element 10, such as shown in FIG. 5.

Thus closing operation of the resilient clamp is made particularly safe and convenient by virtue of the superelevated arrangement of the maneuver portion 11 and of the length of the lever arms of the upper arm 2 and of the lower arm 3.

The closed position is safely and firmly maintained due to the strong elastic reaction applied by the bent elastic branch 5, which appreciably reduces any risks of undesired or accidental opening. This risk is further reduced by the superelevated maneuver portion 11 acting as a front cover protection for the anchoring member 6.

In the closed position shown in FIG. 5 a hose T, fitted such as previously clarified through the body 1 of the resilient clamp, is clamped and throttled between the clamping projections 7 and 12, located in a mutually proximal position. Therefore the flow of an infusion or transfusion fluid through the hose T is throttled as long as the clamp remains in its closed position.

To bring the clamp again to its open position it is sufficient to apply an outward thrust against the anchoring member 6 so as to disengage it, following outward deflection of the bent elastic branch 5, from the anchoring element 10. The upper arm 2 thus returns to the position depicted in FIGS. 1 through 4 following elastic return of the curved end portion 4 to its indeformed condition. This produces displacement of the clamping projections 7 and 12 to their mutually distal position, so as to release the fluid flow through the flexible hose T.

The variant of the invention shown in FIGS. 6 through 9 is generally similar to the embodiment previously disclosed with reference to FIGS. 1 through 5, and only the differences will now be disclosed in detail, using the same numeral references for identical or similar parts.

In spite of the reduced drawing scale, this variant is related to a resilient clamp having a greater size, i.e. having a global length of more than 30 mm. In this clamp the superelevated arrangement of the maneuver portion 11 of the upper arm 2, the length of the lever arms of the upper and lower arms 2,3 between the clamping projections 12,7 thereof and the anchoring element 10 and the bent elastic branch 5, respectively, as well as the acute angle inclination in the undeformed condition of the elastic branch 5 relative to the lower arm 3 are same as in the case of the first disclosed embodiment.

The peculiar difference consists of that in this variant the top of the clamping projection 7 of the lower arm 3, designated as 17, is flat.

Moreover, in consideration of the greater clamp size, the curved end portion 4 is not wider than the upper and lower arms 2,3.

It is to be pointed out that, in both embodiments of the resilient clamp according to the invention as disclosed in the above, sharp edges are substantially totally avoided, since both the longitudinal and the transverse edges of the body 1 are generally bevelled or rounded.

Naturally the details of construction and the embodiments may be widely varied with respect to what has been disclosed and illustrated, without thereby departing from the scope of the present invention such as defined in the appended claims.

What is claimed is:

1. A resilient clamp for closing flexible hoses of infusion, transfusion and the like equipment, comprising a body forming in one single piece an upper arm, a lower arm and a curved end portion having a substantially semi-circular shape and elastically interconnecting said upper and lower arms, wherein said lower arm has on the side opposite to said curved end portion of said body an elastic branch bent towards said upper arm and having an anchoring member, and said upper arm is provided, also on the side opposite to said curved end portion of said body, with a maneuver portion and an anchoring element complementary to said anchoring member of said elastic branch of said lower arm and releasably engageable with said anchoring member, said upper and lower arms being further formed with respective clamping projections facing towards the inside of said body and displaceable between a mutually distal position, corresponding to disengaged condition between said anchoring member and said anchoring element, and a mutually proximal position, corresponding to an engaged condition between said anchoring member and said anchoring element, wherein said curved end portion of said body and said elastic branch of said lower arm are formed with respective apertures defining a passageway for a flexible hose fitted through said body between said upper and lower arms, said maneuver portion of said upper arm is raised with respect to said anchoring element to protect the anchoring member from accidental disengagement from the anchoring element, and wherein at least a portion of the maneuver portion is raised with respect to said anchoring member.

2. Clamp according to claim 1, wherein a curved section is provided between said lower arm and said bent elastic branch thereof, said curved section having a curvature radius such that said bent elastic branch forms with said lower arm, in an undeformed condition, an acute angle.

3. Clamp according to claim 2, wherein said curved section has an outer surface and an inner surface having respectively a greater and, a lower curvature radius.

4. Clamp according to claim 1, wherein the distance between said clamping projection of said upper arm and said anchoring element is substantially greater than the distance between said clamping projection of said upper arm and said curved end portion of said body.

5. Clamp according to claim 4, wherein the distance between said clamping projection of said lower arm and said bent elastic branch thereof is substantially greater than the distance between said clamping projection and said curved end portion of said body.

6. Clamp according to claim 1, wherein said clamping projection of said lower arm has a substantially flat top surface and said clamping projection of said upper arm has a substantially rounded top surface.

7. Clamp according to claim 1, wherein said curved end portion of said body has a width greater than the width of said upper and lower arms.

* * * * *